United States Patent [19]

Baer et al.

[11] Patent Number: 4,520,125

[45] Date of Patent: May 28, 1985

[54] CATALYST FOR THE PREPARATION OF METHYL METHACRYLATE

[75] Inventors: Karl Baer, Weinheim; Peter Bassler, Hirschberg; Gerd Duembgen, Dannstadt-Schauernheim; Gerd Fouquet, Neustadt; Richard Krabetz, Kirchheim; Franz Merger, Frankenthal; Friedbert Nees, Stutensee, all of Fed. Rep. of Germany

[73] Assignee: BASF Aktiengesellschaft, Ludwigshafen, Fed. Rep. of Germany

[21] Appl. No.: 582,727

[22] Filed: Feb. 23, 1984

[30] Foreign Application Priority Data

Feb. 26, 1983 [DE] Fed. Rep. of Germany ....... 3306907

[51] Int. Cl.$^3$ .................... B01J 31/04; B01J 23/62; C07C 67/00; C07C 69/54
[52] U.S. Cl. .................................. 502/170; 502/226; 502/329; 560/208; 560/210; 560/238
[58] Field of Search ............... 502/226, 170, 329, 339, 502/343; 560/208

[56] References Cited

U.S. PATENT DOCUMENTS

| 2,681,938 | 6/1954 | Lindlar | 502/339 |
| 3,827,972 | 8/1974 | Kominami et al. | 502/226 |
| 3,917,676 | 11/1975 | Kisaki et al. | 502/339 |
| 4,249,019 | 2/1981 | Tamura et al. | 560/208 |
| 4,276,200 | 6/1981 | Wu et al. | 502/343 |

FOREIGN PATENT DOCUMENTS

| 54-73717 | 6/1979 | Japan | 502/339 |
| 55-24106 | 2/1980 | Japan | 502/170 |

Primary Examiner—P. E. Konopka
Attorney, Agent, or Firm—Oblon, Fisher, Spivak, McClelland & Maier

[57] ABSTRACT

Catalysts for the preparation of carboxylates from an aldehyde and an alkanol in the presence of oxygen, which contain palladium and lead as active components, these being present on a carrier containing zinc oxide, and the palladium being applied as a palladium salt in a solution containing hydrochloric acid and then being liberated by reduction, and whose carrier consists solely of zinc oxide, are particularly active and selective.

1 Claim, No Drawings

CATALYST FOR THE PREPARATION OF METHYL METHACRYLATE

The preparation of carboxylates from an aldehyde and an alkanol in the presence of oxygen under the action of catalysts is a process which has been worked on by a number of people for some time. A large variety of catalysts has been proposed for this process, among which in particular those which contain palladium as the active constituent are of interest. However, the catalysts of this type which have been disclosed hitherto do not as yet completely satisfy all the requirements set, especially when they are used for the preparation of esters of $\alpha,\beta$-olefinically unsaturated aliphatic carboxylic acids, such as, in particular, methyl methacrylate (also referred to as MMA below).

U.S. Pat. No. 3,772,381 discloses that the reaction of $\alpha,\beta$-olefinically unsaturated aliphatic aldehydes with lower monohydric primary or secondary alkanols and molecular oxygen to give esters of the corresponding carboxylic acids can be carried out using metallic palladium as a catalyst; the palladium may be applied on a suitable carrier, in particular alumina or silicon dioxide. This catalyst has the disadvantage that it gives substantial amounts of by-products (27% by weight of methyl formate and 18% by weight of formaldehyde, the percentages being based on methyl methacrylate). Moreover, only low conversions or poor selectivities are achieved, 3.58 moles of methacrolein per liter of catalyst per hour giving only 0.11 mole of methyl methacrylate per liter of catalyst per hour (cf. Example 4 of that publication).

U.S. Pat. No. 3,639,449 describes a very similar process for the preparation of carboxylates from aldehydes and/or alkanols by reaction with oxygen over a noble metal catalyst (eg. palladium) at from 0° to 300° C. In this case too, it is evident that a pure palladium catalyst is of little use for the preparation of methyl methacrylate: Example 16, the only one which describes the preparation of methyl methacrylate from methanol and methacrolein over a catalyst (2% of Pd on active carbon), states that the methacrolein conversion is 17.3%, with a selectivity of 56.1% with respect to methyl methacrylate and 40.6% with respect to propylene.

U.S. Pat. No. 4,249,019 discloses a catalyst for the preparation of carboxylates by reaction of an aldehyde with an alkanol in the presence of oxygen at from 0° to 200° C.; this catalyst contains a) palladium b) an oxide, hydroxide, carbonate, nitrate or carboxylate of thallium or mercury and c) an oxide, hydroxide, carbonate or carboxylate of an alkali metal or alkaline earth metal. Although such a catalyst gives high methyl methacrylate selectivities (90-95%), the space-time yield, expressed as the productivity (g of MMA per g of Pd per hour), is unsatisfactory. Furthermore, it should be noted that the values for the productivity in Table 1 of the German Published Application were determined at a low conversion (see the last line of the notes on the Table) and therefore do not give a true picture of the productivity in relation to the overall conversion; the productivity is from 2 to 10.5, based on the overall conversion to methyl methacrylate.

Prior U.S. Patent Application Ser. No. 473,601 relates to a catalyst which contains palladium and lead as active components, these being present on a carrier which contains two or more oxides from among ZnO, $Al_2O_3$, $La_2O_3$ and $TiO_2$, and the catalyst being virtually free from alkali metal compounds and alkaline earth metal compounds. The palladium is applied onto the carrier preferably in the form of a palladium chloride solution which contains hydrochloric acid, and is reduced there to metallic palladium. In this way, the abovementioned disadvantages can be overcome. Instead of palladium chloride, it is also possible to use another salt of palladium, in particular a water-soluble salt, eg. the nitrate, acetate or sulfate, or a complex salt, such as tetraminepalladium chloride. We have found that catalysts for the preparation of carboxylates from an aldehyde and an alcohol in the presence of oxygen, which contain palladium and lead as active components, these being present on a carrier containing zinc oxide, and the palladium being applied as a palladium salt from a solution containing hydrochloric acid and then being liberated by reduction, are particularly active and selective if the carrier consists solely of zinc oxide. The novel catalysts give, for example at conversions of about 75% and selectivities of about 86%, productivities of from 6.5 to 7 g of methyl methacrylate per g of palladium per hour; at a conversion of 65% and a selectivity of 91%, the productivity has increased to about 10 g of methyl methacrylate per g of Pd per hour. If, when using the novel catalyst, a conversion of less than 70%, eg. 65% or less, is employed, a preferred procedure for the reaction is a 2-stage one in which, for example, two reactors are connected in succession so that the reacted mixture from the first reactor, after further methacrolein is added, is fed to the second reactor, in which the mixture is then oxidized further.

Commercial zinc oxide, for example in the form of small commercially available cylinders of 2-8 mm length and 2-4 mm diameter, can be used as the carrier for the novel catalysts. It is also possible to use commercial $Zn(OH)_2ZnCO_3$, which is calcined at from 200° to 800° C., in particular from 300° to 500° C., and then molded to small cylinders, for example with a length of 2-8 mm and a diameter of 2-8 mm. Molded particles of zinc oxide which have a BET specific surface area of from 10 to 100 $m^2/g$ are of particular interest for the preparation of the catalysts. The method of determining the BET surface area is described by R. Haul and G. Dumbgen in Chem.-Ing.-Technik 35 (1963), 586-589. The pre-molded ZnO carrier material, eg. the small cylinders, contain the palladium in metallic form in an amount of in general from 0.1 to 10, preferably from 0.2 to 5, particularly preferably from 0.3 to 2, % by weight, based on the total weight including the carrier. It is also possible for the catalyst to contain lead in metallic form or in the form of lead compounds in an amount of from 0.1 to 20, preferably from 0.2 to 10, in particular from 0.2 to 4, % by weight, calculated as metal and based on the total weight. The catalyst can be prepared in a conventional manner, for example by treating the carrier first with an aqueous solution of palladium chloride with the addition of free hydrochloric acid, and then with an aqueous solution of a lead salt, eg. lead acetate, until the salts have been absorbed by the carrier, and can be treated, either between or after the two impregnation procedures, with a reducing agent, eg. hydrogen or formaldehyde, and the ready-prepared catalyst can finally be dried.

When the ZnO carrier material is treated with an aqueous palladium salt solution containing hydrochloric acid, the solution should contain in general from 0.05 to 10, in particular from 0.1 to 8, % by weight, based on the solution, of free hydrochloric acid. If a palladium salt solution with a lower content of free hydrochloric acid is used, it has proven advantageous to treat the carrier material before it is impregnated with the palladium salt solution, or, if appropriate, also the catalyst particles after reduction of the palladium salt, with dilute hydrochloric acid which preferably has a concentration of from 0.05 to 10, in particular from 0.1 to 8, % by weight.

The novel catalyst can particularly advantageously be used for the preparation of carboxylates, in particular α,β-olefinically unsaturated carboxylates, from the corresponding aldehydes and alkanols in the presence of oxygen. The alkanols can be straight-chain or branched, and in general of 1 to 4 carbon atoms. It can be particularly advantageously used for the preparation of methyl methacrylate from methacrolein, methanol and oxygen at in general from 0° to 100° C., in particular from 30° to 60° C. The reaction can be carried out in the gas phase or, preferably, in the liquid phase.

The catalysts according to the invention can be employed by a batchwise or continuous procedure. Conventional molar ratios of alkanol, in particular methanol, to aldehyde, in particular methacrolein, of from 200:1 to 1:1 have generally proven useful for this reaction. When a batchwise procedure is used, the amount of catalyst is generally chosen to be from 0.2 to 10 times the weight of the aldehyde converted. For a continuous procedure, the amount of catalyst can be as much as 100 times the weight of aldehyde passed through the reaction space per hour, but should be no less than about this amount.

If the reaction of the aldehyde with the alkanol is carried out in the liquid phase, which is preferred, it is possible to add solvents which are inert to the reactants. Examples of suitable solvents are octane, toluene, xylenes and heavy gasoline (boiling range 150°–180° C.). However, the amount of such additional solvents should not in general exceed half the amount of the alkanol employed.

Oxygen is used in the pure molecular form or in the form of a mixture with one or more other gases, in particlar nitrogen or carbon dioxide. For example, air is a suitable source of oxygen. It has proven useful to use the oxygen in an amount greater than that required for the reaction. Preferably, it is used in not less than 1.5 times the stoichiometric amount.

The reaction can be carried out under reduced, atmospheric or superatmospheric pressure, atmospheric pressure generally being preferred.

In the Examples which follow, parts and percentages are by weight. Furthermore, $$\text{Conversion (\%)} = \frac{\text{methacrolein converted, in moles}}{\text{methacrolein fed in, in moles}} \times 100$$

$$\text{Selectivity (\%)} = \frac{\text{methyl methacrylate formed, in moles}}{\text{methacrolein converted, in moles}} \times 100$$

EXAMPLE 1

100 parts of small commercial ZnO cylinders having a specific surface area of from 20 to 30 m$^2$/g, a length of from 4 to 6 mm and a diameter of 4 mm are treated with a solution of 0.84 part of palladium chloride in 500 parts of water (which contains free hydrochloric acid as a result of hydrolysis), while stirring from time to time, until the supernatant solution is clear and colorless.

The water is then decanted, and the ZnO carrier particles which are impregnated with palladium chloride are treated with 500 parts of a 0.5% strength aqueous formaldehyde solution for 4 hours at 60° C. The solution is then decanted, and the catalyst particles are treated for 4 hours with a solution of 0.5 part of lead acetate in 500 parts of water. The water is once again decanted, and the catalyst is dried for 12 hours under nitrogen at 120° C. Analysis shows that the resulting catalyst contains 0.21% by weight of palladium and 0.32% by weight of lead.

100 parts of the catalyst are introduced into a reaction tube which has a length of 0.8 m and a diameter of 1.4 cm and is equipped with a thermostat. The temperature of the reaction tube is kept at 40° C., and 3 parts hour of methacrolein, 27 parts/hour of methanol and 3 parts/hour of oxygen are passed in through the lower end. After an operating time of 24 hours, the conversion is 36%, the selectivity is 85% and the productivity is 6.0 parts of methyl methacrylate per part of Pd per hour, and after an operating time of 120 hours these parameters are 42%, 84% and 7.2 parts, respectively.

EXAMPLE 2

The procedure described in Example 1 is followed, except that 1.2 parts of HCl are added to the palladium chloride solution. The catalyst then obtained, under otherwise identical conditions, contains 0.42% by weight of palladium and 0.38% by weight of lead and, in the conversion of methacrolein with methanol and oxygen and under the conditions stated in Example 1, gives a conversion of 78%, a selectivity of 83% and a productivity of 6.6 parts of methyl methacrylate per part of Pd per hour after 24 hours, these parameters being 74%, 86% and 6.5 parts, respectively, after an operating time of 200 hours.

EXAMPLE 3

The procedure described in Example 1 is followed, except that a palladium chloride solution which contains 1.9 parts of hydrochloric acid is used. A catalyst which contains 0.45% by weight of palladium and 0.31% by weight of lead is then obtained, under otherwise identical conditions.

50 parts of this catalyst are introduced into a reaction tube which has a length of 0.4 m and a diameter of 1.4 cm and is equipped with a thermostat. 3 parts/hour of methacrolein, 27 parts/hour of methanol and 3.0 parts hour of oxygen are fed into the lower end of the reaction tube, which is kept at 45° C. After 24 hours, the conversion is 62%, the selectivity is 84% and the productivity is 8.9 parts of methyl methacrylate per part of Pd per hour, and after an operating time of 120 hours these parameters are 60%, 87% and 9.2 parts, respectively.

EXAMPLE 4

200 parts of small commercial ZnO cylinders having a specific surface area of from 20 to 30 m$^2$/g, a length of from 4 to 6 mm and a diameter of 4 mm are treated with a solution of 1.68 parts of palladium chloride and 3.8 parts of HCl in 1,000 parts of water, while stirring, until the supernatant solution is colorless and clear. The water is decanted, and the remaining catalyst is treated for 4 hours at 60° C. with 1,000 parts of a 0.5% strength aqueous formaldehyde solution. The aqueous phase is separated off, and the catalyst is then treated with a solution of 1 part of lead acetate in 1,000 parts of water for 4 hours at room temperature. The supernatant solution is decanted, and the remaining catalyst is dried for 12 hours at 120° C. under nitrogen. The resulting catalyst contains 0.42% of palladium and 0.32% of lead.

65 parts of this catalyst are introduced into a reaction tube (reactor 1) which has a length of 0.6 m and a diameter of 1.4 cm and is equipped with a thermostat. This reactor 1 is connected, via an overflow, to the lower end of a reactor 2, which is equipped in the same way as reactor 1 and contains 65 parts of the catalyst. 3 parts hour of methacrolein, 57 parts/hour of methanol and 3 parts/hour of oxygen are then fed into the lower end of reactor 1 at 40° C. 3 parts/hour of methacrolein are added to the reacted mixture from reactor 1, and this mixture is then fed, with the addition of 2 parts/hour of oxygen, continuously into the lower end of reactor 2, which is at 40° C. After 24 hours, the conversion is 68%, the selectivity is 89% and the productivity is 8.9 g of methyl methacrylate per part of Pd per hour, and after 170 hours these parameters are 65%, 91% and 9.3 g, respectively.

EXAMPLE 5

65 parts of the catalyst described in Example 4 are introduced into a reaction tube which has a length of 0.6 m and a diameter of 1.4 cm and is equipped with a thermostat. 3 parts/hour of methacrolein, 27 parts/hour of methanol and 3 parts/hour of oxygen are fed into the lower end of the reaction tube, which is kept at 40° C. After 24 hours, the conversion is 65%, the selectivity is 88% and the productivity is 8.3 parts of methyl methacrylate per part of Pd per hour, and after an operating time of 170 hours these parameters are 66%, 79% and 8.3 g, respectively.

EXAMPLE 6

500 parts of commercial $Zn(OH)_2.ZnCO_3$ are calcined for 12 hours at 500° C. and then mixed with 200 parts of water for 1 hour in a kneader, andd the mixture is converted to extrudates having a diameter of 3 mm and a length of from 4 to 8 mm. These are then dried for 2 hours at 200° C., for 2 hours at 400° C. and for 2 hours at 500° C. The procedure described in Example 3 is followed, and a catalyst which contains 0.49% by weight of palladium and 0.40% by weight of lead is then obtained, under otherwise identical conditions.

50 parts of this catalyst are introduced into a reaction tube which has a length of 0.5 m and a diameter of 1.4 cm and is provided with a thermostat. 3 parts/hour of methacrolein, 27 parts/hour of methanol and 3 parts hour of oxygen are fed into the lower end of the reaction tube, which is kept at 40° C. After 24 hours, the conversion is 59%, the selectivity is 90% and the productivity is 9.1 parts of methyl methacrylate per part of Pd per hour, and after an operating time of 170 hours these parameters are 60%, 91% and 9.1 parts, respectively.

We claim:

1. In a catalyst for the preparation of a carboxylate from an aldehyde and an alkanol in the presence of oxygen, which as active components consists essentially of palladium and lead, these being present on a carrier containing zinc oxide, and the palladium being applied as a palladium salt in a solution containing hydrochloric acid and then being liberated by reduction and the lead being applied as lead acetate, wherein said palladium is present in a range of 0.1–10% by weight and said lead is present in a range of 0.1–20% by weight, both calculated as metal as a percentage of the total weight of the catalyst and carrier, the improvement being that the carrier consists solely of zinc oxide.

* * * * *